United States Patent

Sato et al.

[11] Patent Number: 5,573,779
[45] Date of Patent: Nov. 12, 1996

[54] LIPOSOME COMPOSITION

[75] Inventors: Shuji Sato; Iwao Nozawa; Katsuhiko Akiyama, all of Tsukuba, Japan

[73] Assignee: Hisamitsu Pharmaceutical Co., Inc., Tosu, Japan

[21] Appl. No.: 313,231

[22] PCT Filed: Apr. 9, 1993

[86] PCT No.: PCT/JP93/00460

§ 371 Date: Sep. 30, 1994

§ 102(e) Date: Sep. 30, 1994

[87] PCT Pub. No.: WO93/20801

PCT Pub. Date: Oct. 28, 1993

[30] Foreign Application Priority Data

Apr. 10, 1992 [JP] Japan .................................. 4-118025

[51] Int. Cl.$^6$ ........................................................ A61K 9/127
[52] U.S. Cl. ............................................ 424/450; 436/829
[58] Field of Search ............................... 424/450; 436/829

[56] References Cited

U.S. PATENT DOCUMENTS

| 4,920,016 | 4/1990 | Allen | 424/450 |
| 4,952,405 | 8/1990 | Young | 424/423 |
| 5,100,662 | 3/1992 | Bolcsak | 424/88 |

FOREIGN PATENT DOCUMENTS

| 502590 | 9/1989 | Japan . |
| 236325 | 10/1991 | Japan . |

Primary Examiner—Gollamudi S. Kishore
Attorney, Agent, or Firm—Bucknam and Archer

[57] ABSTRACT

A liposome composition which is effective in administering a physiologically active substance to Peyer's patches and is characterized by containing phosphatidylcholine, cholesterol and phosphatidylinositol as lipid components and having a high ability to migrate into Peyer's patches.

1 Claim, 1 Drawing Sheet

LIPOSOME COMPOSITION

FIELD OF THE INVENTION

This invention relates to a liposome composition for forming liposomes which are artificial lipid membranes mainly comprising phospholipids. More particularly, it relates to a liposome composition which is effective in administering a physiologically active substance to Peyer's patches (Peyer's glands).

BACKGROUND OF THE INVENTION

A Peyer's patch, which is an aggregate of lymph nodules covered with thin epithelial cells and exists in the jejunum or ileum, was reported by Peyer in 1677. It is one of protective organs against exogenous antigens such as bacteria. This protective system in the digestive tract mainly comprises secretory IgA (immunoglobulin A) produced and secreted in the intestinal mucosa. The production of this secretory IgA is controlled by the intestinal lymphoid tissue including Peyer's patches. This intestinal lymphoid tissue, which consists of the above-mentioned Peyer's patches, mesenteric lymph nodes, lamina propria mucosae, interepithelial cellular lymphocytes and plasma cells, is responsible for the local immunity independent of the systemic immunity. The epithelial cells involve chorioepithelium analogous to resorption epithelial cells and M cells (microholed cells) having thick and short microvilli. M cells, which were reported by Owen et al. in 1974, are now considered as an entrance into the digestive tract for exogenous antigens [Gastroenterology, 66, 189–203 (1974)].

Among antigens existing in the digestive tract, a specific one is selectively taken up or seized by M cells and the information thereof is transmitted to T cells via antigen presenting cells. The T cells comprise Th as the main component and the function thereof is controlled under the influences of various cytokines. The information of the antigen is further transmitted to B cells which will then differentiate into antibody-forming plasma cells. On the other hand, it is known that when a large amount of an antigen exists in the digestive tract for a prolonged period of time, an immunologically tolerant state is induced in the systemic immunity system via the function of suppressor T cells induced in Peyer's patches. Therefore it can be said that Peyer's patches play an important role not only in the local immunity but also in the systemic immunity.

Peyer's patches, which have the above-mentioned functions and are considered as the entrance of a route directly connected to the lymphatic system, may be regarded as the target sites of an immunomodulator such as an immunosuppressant or an immunopotentiator, an oral vaccine (a vaccine for oral administration), or an antigen aiming at oral desensitization (an attempt to reduce sensitization by oral administration).

As a conventional method for the administration of a physiologically active substance to Peyer's patches, there is known a method wherein are used hydrophobic and in vivo-degradable polymers such as in vivo-degradable polyesters (Japanese Patent Application Laid-Open Gazette No. 190833/88). This method comprises a technique for preparing microcapsules from a mixed solution of a high-molecular substance and a physiologically active substance which are dissolved in an organic solvent, by a submerged drying method. However, the physiologically active substances to be used for the above-mentioned purposes involve many hydrophilic substances such as polypeptides. Accordingly, the submerged drying method as described in the above Gazette is disadvantageous in that microcapsules having these hydrophilic substances encapsulated therein can be hardly prepared thereby.

It is an object of the present invention to provide a liposome composition whereby both of hydrophobic and hydrophilic physiologically active substances can be encapsulated and which has a high ability to migrate toward Peyer's patches.

SUMMARY OF THE INVENTION

The present inventors have conducted an extensive study of a drug carrier which has a high ability to migrate toward Peyer's patches and in which hydrophilic drugs such as physiologically active peptides and hydrophobic drugs such as steroids can be encapsulated. As the result of their study, they have successfully found out that the ability of a specific liposome to migrate toward Peyer's patches can be improved by adding phosphatidylinositol to the specific liposome. Additionally, they have found out that the above-mentioned ability can be further improved by virtue of the synergistic effect achieved by adding phosphatidylserine together with phosphatidylinositol to the above-mentioned liposome.

The present invention, which has been completed based on these findings, relates to a liposome composition which can solve the problem of the encapsulation of a hydrophilic physiologically active substance and enables a physiologically active substance to be effectively administered to Peyer's patches although said problem of encapsulation can hardly be solved by the conventional method for the administration of a physiologically active substance to Peyer's patches with the use of a hydrophobic and in vivo-degradable polymer spherules.

The liposome composition of the present invention is one which has a high ability to migrate toward Peyer's patches and is characterized by containing phosphatidylcholine, cholesterol and phosphatidylinositol as lipid components.

Among the lipid components to be used in the present invention, the fundamental components other than phosphatidylinositol are not particularly restricted, though it is preferable to use phosphatidylcholine and cholesterol in order to achieve a high ability to form liposomes. The phosphatidylcholine according to the present invention is not particularly restricted and includes soybean phosphatidylcholine, yolk phosphatidylcholine, hydrogenated phosphatidylcholine, dipalmitoylphosphatidylcholine or distearoylphosphatidylcholine with hydrogenated phosphatidylcholine, dipalmitoylphosphatidylcholine or distearoylphosphatidylcholine being preferred. The molar ratio of phosphatidylcholine to cholesterol ranges preferably from 7/0.5 to 7/7, more preferably from 7/1 to 7/3.

In addition to the fundamental lipids as described just above, the liposome composition of the present invention essentially contains phosphatidylinositol as a lipid component. When the liposome composition contains phosphatidylinositol, its ability to migrate toward Peyer's patches is improved. The content of the above-mentioned phosphatidylinositol ranges preferably from 0.1 to 50% by mol in the total amount of the lipid components. When its content is less than 0.1% by mol, there is a tendency that the effect of the addition thereof cannot be fully achieved. When this content exceeds 50% by mol there is a tendency that no sufficient stability of the resulting liposomes can be obtained. The phosphatidylinositol according to the present invention is not particularly restricted and is exemplified by soybean phosphatidylinositol or bovine brain phosphatidylinositol. Further, phosphorylated derivatives thereof such as phosphatidylinositol 4,5-diphosphate and phosphatidylinositol 4-monophosphate are usable as well.

It is preferable that the liposome composition of the present invention further contains phosphatidylserine as a lipid component in addition to the above-mentioned phosphatidylinositol. When the liposome composition contains phosphatidylserine together with phosphatidylinositol, its ability to migrate toward Peyer's patches is furthermore improved by the synergistic effect of these components. The content of the phosphatidylserine ranges preferably from 0.1 to 50% by mol in the total amount of the lipid components. When its content is less than 0.1% by mol, there is a tendency that the effect of the addition thereof cannot be fully achieved. When this content exceeds 50% by mol, there is a tendency that no sufficient stability of the resulting liposomes can be obtained.

Although the liposome composition of the present invention may consist of the above-mentioned lipids, it may contain additional lipids such as other phospholipids, glycolipids and fat-soluble vitamins in addition to the above-mentioned lipid components, and, furthermore, it may contain components other than lipids. When the liposome composition of the present invention contains components other than the above-mentioned lipid components, it is preferable that the content of the above-mentioned lipid components be 50% by weight or more based on the total amount of the composition. When the content of the components other than the above-mentioned lipid components exceeds 50% by weight, there is a fear that the liposomes thus obtained become unstable.

When the above-mentioned liposome composition of the present invention is used, hydrophobic physiologically active substances such as steroids and hydrophilic physiologically active substances such as physiologically active peptides can be easily encapsulated therein irrespective of the type thereof, which makes it possible to easily and efficiently prepare liposomes having the desired components such as these active substances encapsulated therein.

A method for preparing liposomes from the liposome composition of the present invention is not particularly restricted and such liposomes can be easily prepared by any conventional method. For example, phosphatidylcholine, cholesterol and phosphatidylinositol optionally together with phosphatidylserine, each in a given amount, are dissolved in chloroform thereby to obtain a chloroform solution. When a hydrophobic physiologically active substance is to be encapsulated in the to-be-obtained liposomes, the hydrophobic physiologically active substance is dissolved in chloroform together with the above-mentioned lipids. Next, this chloroform solution is evaporated to dryness in an eggplant type Flask thereby to obtain a lipid film as a coating Formed on the inner wall of the flask. Then a Trishydrochloric acid buffer is introduced into the flask. When a hydrophilic physiologically active substance is to be encapsulated in the to-be-obtained liposomes, the hydrophilic physiologically active substance is previously dissolved in the above-mentioned buffer. Then the contents of the flask are subjected to a vortex or ultrasonic treatment thereby to obtain a solution containing liposomes. Further, liposomes having the desired particle size can be obtained by filtering the liposome solution obtained above.

The liposome composition of the present invention is applicable to the administration (for example, oral administration) of any physiologically active substance which can be expected to achieve a high pharmacological effect by administration to Peyer's patches. For example, an oral desensitizing preparation, an oral vaccine preparation or an immunomodulator preparation to be administered to Peyer's patches can be prepared by forming liposomes which have an oral desensitizing antigen, an oral vaccine or an immunomodulator encapsulated therein with the use of the liposome composition of the present invention. As described above, a hydrophilic physiologically active substance can be encapsulated in the liposome composition of the present invention, and, therefore, the liposome composition of the present invention is applicable to the administration of a physiologically active peptide which is difficulty absorbable and degradable when orally administered. The absorbability and non-degradability of the physiologically active peptide can be improved by orally administering the physiologically active peptide encapsulated in liposomes prepared from the liposome composition of the present invention. The above-mentioned oral desensitization means a method which comprises inducing immunological tolerance by orally administering an allergen thereby to suppress an allergic reaction which is a hyperimmune reaction. The function of Peyer's patches which controls the local immunity in the digestive tract closely relates to the oral desensitization.

As described above, the component which can be encapsulated in the liposome composition of the present invention is not particularly restricted. Thus any desired physiologically active substance to be administered to Peyer's patches can be encapsulated in said liposome composition. The allergens which can be encapsulated in the liposome composition of the present invention and are administered for the purpose of oral desensitization include any causative allergens employed in the desensitization therapy in the field of dermatology at the present stage, such as mite extract and mite antigen which are said to be the main component of house dust, cedar pollen which is an antigen causing cedar pollinosis, and egg albumin which is a food allergen. In the case of an oral vaccine, it is assumed that the immunization with the vaccine should be effected via Peyer's patches. Thus the liposome composition of the present invention is applicable to the administration of various vaccines. The immunomodulators which can be encapsulated in the liposome composition of the present invention include cytokines such as interferon and interleukin-2, immunopotentiators such as muramyldipeptide, and immunosuppressors such as steroids.

FUNCTION

The liposome composition of the present invention comprises the fundamental lipids which are phosphatidylcholine and cholesterol, and phosphatidylinositol added thereto. Thus the liposomes prepared from this composition show an extremely high ability to migrate into Peyer's patches. By further adding phosphatidylserine to the above-mentioned composition, a synergistic effect is achieved and thus the above-mentioned ability to migrate is further improved.

BEST MODE FOR CARRYING OUT THE INVENTION

To illustrate the present invention in greater detail, the following Examples will be given.

EXAMPLES 1 TO 5 AND COMPARATIVE EXAMPLES 1 to 3

The composition of each of the liposome compositions of the Examples and Comparative Examples is indicated in Table 1.

TABLE 1

|  | DPPC | Chol | PI | DCP | PS |
|---|---|---|---|---|---|
| Example 1 | 12.6 | 5.4 | 1.8 | — | — |
| Example 2 | 12.6 | 5.4 | 5.4 | — | — |
| Example 3 | 12.6 | 5.4 | 9.0 | — | — |
| Example 4 | 12.6 | 5.4 | 0.9 | — | 0.9 |
| Comp. Ex. 1 | 12.6 | 5.4 | — | — | — |
| Comp. Ex. 2 | 12.6 | 5.4 | — | 9.0 | — |
| Example 5 | 12.6 | 5.4 | 0.9 | — | — |
| Comp. Ex. 3 | 12.6 | 5.4 | — | — | 0.9 |

Unit; μmol

*The abbreviations in Table 1 stand for the following.
DPPC: dipalmitoylphosphatidylcholine;
Chol: cholesterol;
PI: phosphatidylinositol;
DCP: dicetyl phosphate; and
PS: phosphatidylserine.

[Preparation of radioactive-labeled liposomes for use for the evaluation of their ability to migrate into Peyer's patches]

25 μCi of $^3$H-labeled cholesteryl oleate and the lipid components, each in the amount as specified in Table 1, were introduced into an eggplant type Flask (50 ml) and incorporated with 5 ml of chloroform to dissolve the above lipid components therein, after which the chloroform was evaporated with the use of an evaporator thereby to obtain a lipid film on the inner wall of the flask. Next, 10 ml of a 0.01M Trishydrochloric acid buffer was introduced into the flask and the film was redispersed in the buffer by ultrasonic treatment thereby to obtain a solution containing liposomes. The liposome solution thus obtained was filtered through a 0.45 μm membrane filter thereby to obtain a liposome sample.

Table 2 shows the results of the measurement of the ζ-potentials (zeta potentials) of the liposomes thus obtained.

TABLE 2

|  | Zeta potential (mV) |
|---|---|
| Example 1 | −10.6 |
| Example 2 | −16.7 |
| Example 3 | −29.9 |
| Comp. Ex. 1 | −4.1 |
| Comp. Ex. 2 | −35.1 |

[Extraction of biological specimens for use for the evaluation of the ability to migrate into Peyer's patches]

In order to evaluate liposomes for their ability to migrate into Peyer's patches in vitro, a rabbit intestinum tenue Peyer's patch sample was prepared in the following manner. Under urethane-anesthesia, the intestinum tenue of a male NZW rabbit aged 8 weeks was extracted. By using a punch of 10 mm in diameter, Peyer's patch sites (5 sites per rabbit on the average) and non-Peyer's patch sites therearound were punched out. These tissue pieces thus punched out were suspended in 6 ml of an RPMI-1640 medium and used as the specimens for use for the evaluation of the ability to migrate into Peyer's patches.

[Experiment in vitro on the ability of liposome to migrate into Peyer's patches]

Figure 1:
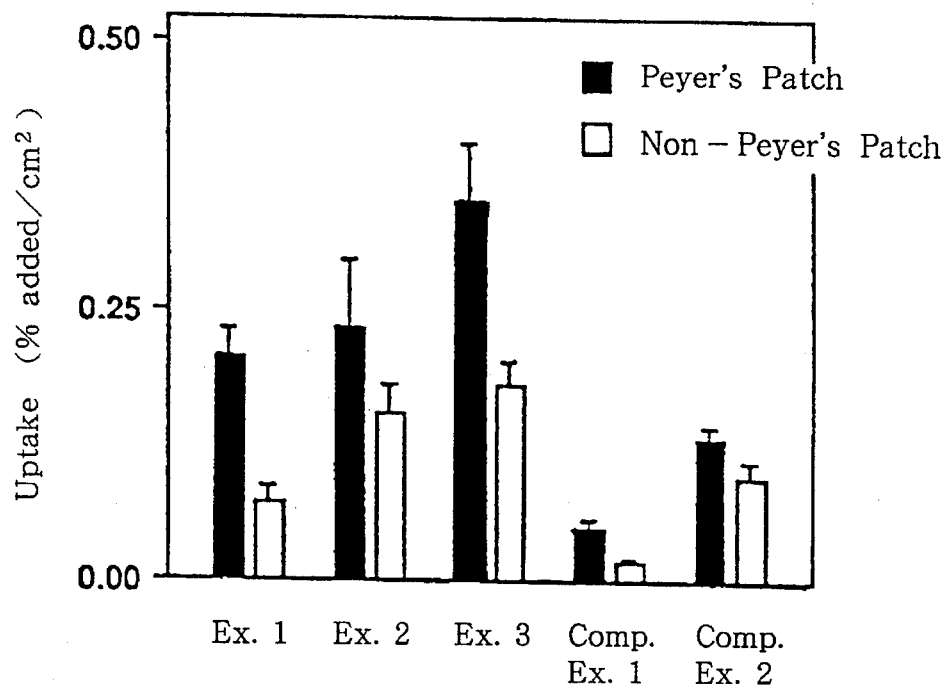
FIG. 1 is a graph which shows the effect of phosphatidylinositol on the uptake of liposomes into Peyer's patches.
Figure 2:
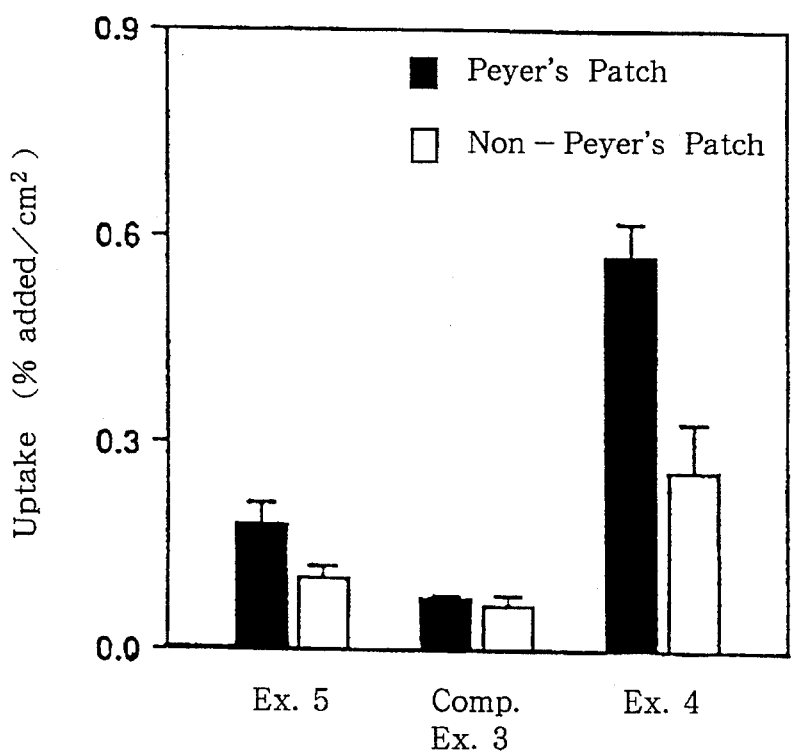
FIG. 2 is a graph which shows the synergistic effect of phosphatidylinositol and phosphatidylserine on the uptake of liposomes into Peyer's patches.

To the liquid in which the Peyer's patch and non-Peyer's patch tissue pieces were suspended, was added the above-mentioned liposome solution in such a manner as to give a final lipid concentration of 100 nmol/ml. After being allowed to stand in a $CO_2$ incubator for 2 hours, the resulting mixture was centrifuged at 1,000 rpm at 4° C., freed from the supernatant liquid, and then incorporated with a fresh RPMI-1640 medium thereby to effect washing. After washing again in the same manner as mentioned above, the tissue pieces were each solubilized with a tissue resolvent. Subsequently, each of the solubilized tissues was incorporated with a scintillator solution and the radioactivity of the liquid thus obtined was directly measured with a liquid scintillation counter as an indication of the liposome uptake. FIGS. 1 and 2 show the results thus obtained.

FIG. 1 shows the effect of phosphatidylinositol on the ability of liposomes to migrate into Peyer's patches. The liposomes of Comparative Example 1 consisting of dipalmitoylphosphatidylcholine and cholesterol showed an insufficient ability to migrate into Peyer's patches. However, the ability was largely elevated by adding phosphatidylinositol as a lipid constituting the liposome membrane (Example 1). The ability to migrate into Peyer's patches was further elevated with an increase in the content of phosphatidylinositol in the lipid membrane.

On the other hand, liposomes containing dicetyl phosphate which is an acidic phospholipid similar to phosphatidylinositol, had a higher negative charge (Table 2) than those containing phosphatidylinositol but effected no significant migration to Peyer's patches. These facts suggest that the high ability to migrate into Peyer's patches of the liposomes containing phosphatidylinositol as a lipid constituting the membrane have been achieved via some recognition system other than the zeta potential.

FIG. 2 shows the synergistic effect obtained by further adding phosphatidylserine to liposomes containing phosphatidylinositol in the lipid membrane. Compared with the liposomes containing phosphatidylinositol and free of phosphatidylserine (Example 5) and those containing phosphatidylserine and free from phosphatidylinositol, Comparative Example 3, the liposomes of Example 4 containing phosphatidylserine together with phosphatidylinositol showed a synergistically elevated ability to migrate into Peyer's patches.

[Industrial Applicability]

As described above, the liposome compositions of the present invention, which contain phosphatidylinositol optionally together with phosphatidylserine in addition to phosphatidylcholine and cholesterol, show an extremely high ability to migrate into Peyer's patches. By using the liposome compositions of the present invention, hydrophobic and hydrophilic physiologically active substances can be encapsulated therein.

Therefore, use of liposomes in which physiologically active substances are encapsulated with the use of the liposome compositions of the present invention makes it possible to obtain oral desensitizing preparations, oral vaccine preparations and immunomodulator preparations, which contain a hydrophilic drug, to be administered to Peyer's patches. Furthermore, it is expected that remarkable pharmacological effects can be achieved by using these preparations.

We claim:

1. The method of treatment of a living subject in need of a hydrophilic or hydrophobic physiologically substance active on migrating to the aggregate of lymph nodules present in the jejunum or ileum called Peyer's glands, said physiologically active substance is asteroid, muramyldipeptide, interferon, interleukin-2, mite antigen or cedar pollen antigen, which consists of administering orally to said living subject a liposome composition migrating to the Peyer's glands of a living subject, which consists essentially of (a) four lipid components consisting of 1) dipalmitoylphosphatidylcholine, 2) cholesterol, 3) phosphatidylinositol and 4) phosphatidylserine, wherein the molar ratio of said component 1) to component 2) ranging from 7:0.5 to 7:7, and the contents of said components 3) and 4) are each from 0.1 to 50% by mol of the total amount of said four lipid components; and (b) a physiologically active substance encapsulated in said liposomes which is a steroid, muramyldipeptide, interferon, interleukin-2, mite antigen or cedar pollen antigen.

* * * * *